United States Patent [19]

Hunting

[11] Patent Number: 5,080,583
[45] Date of Patent: Jan. 14, 1992

[54] FRAGRANCED ORTHODONTIC APPLIANCE AND METHOD OF MAKING

[76] Inventor: Tanya L. Hunting, 1013 E. Third St., Royal Oak, Mich. 48067

[21] Appl. No.: 572,036

[22] Filed: Nov. 23, 1990

[51] Int. Cl.⁵ .............................................. A61C 3/00
[52] U.S. Cl. .......................................... 433/2; 433/6; 264/16
[58] Field of Search .................. 433/2, 6, 8; 264/16

[56] References Cited

U.S. PATENT DOCUMENTS

| | | | |
|---|---|---|---|
| 3,421,221 | 1/1969 | Silverman et al. | 433/23 |
| 3,600,807 | 8/1971 | Sipos | 433/167 |
| 3,808,686 | 5/1974 | Tauman et al. | 433/168.1 |
| 3,941,858 | 3/1976 | Shepherd et al. | 260/885 |
| 4,568,560 | 2/1986 | Schobel | 426/3 |
| 4,676,752 | 6/1987 | Lefkowitz | 433/229 |
| 4,741,700 | 5/1988 | Barabe | 433/229 |
| 4,791,156 | 12/1988 | Hostettler | 528/76 |

Primary Examiner—John J. Wilson
Attorney, Agent, or Firm—Basile and Hanlon

[57] ABSTRACT

The fragranced orthodontic appliance and method of making the same utilizes a fragranced "cold cure" acrylic. The method comprises the steps of combining fragrancing oils in a predetermined ratio with a monomer liquid. The monomer is then combined in a conventional manner with a polymer to form a hard acrylic orthodontic appliance. The appliance includes a hard cold cure acrylic base member which is formed from a suitable powdered polymeric component and a liquid monomeric component, the liquid monomeric component containing a selected fragrancing oil therein. The method comprises the steps of admixing an effective amount of fragrancing oil with a liquid monomeric component and then admixing the resulting mixture with an effective amount of a powdered polymeric component to form an acrylic base member. Hardware is then embedded in the acrylic base member.

5 Claims, No Drawings

FRAGRANCED ORTHODONTIC APPLIANCE AND METHOD OF MAKING

BACKGROUND OF THE INVENTION

1. Technical Field

This invention relates to orthodontic appliances.

2. Background Art

Anyone who has had orthodontic treatment knows the discomfort associated with the wearing of an orthodontic appliance, such as a retainer. They are bulky and often impede clear speech. Exposed wires can also be an embarrassment, especially to younger people. Habitual wearing of the appliance is required, however, in order to achieve the desired results.

An orthodontic appliance consists of wires and auxiliary devices imbedded in a hard acrylic resin which conforms to the upper or lower palate of the mouth. Some such appliances are: Frankel, Bionator, Retainer, Sagittal, and Bonded Palatal Expander, etc. They are unlike other dental prosthesis in that they are made with what is commonly known in the art as "cold cure" acrylic.

Acrylic is made up of two substances: a polymeric component and a monomeric component. To produce the desired acrylic material, the polymer is used as a powdered compound and the monomer is used as a liquid compound.

A variety of dental prosthetic devices have been proposed. To ease wear discomfort, it has been proposed that the acrylic material be flavored or scented heretofore. This has required the complex addition of flavoring or olfactory agents to the polymeric component or the spraying of a surface coating of a scented solution onto the prepared acrylic device.

SUMMARY OF THE INVENTION

The present invention is a fragranced orthodontic appliance and method of making the same which ameliorates the discomfort experienced by the patient by an appliance which has a pleasant taste and smell. The appliance of the present invention comprises a hard cold cure acrylic base member adapted to conform and contour to the associated palate region of the patient's mouth and associated metallic hardware in contact with the patient's teeth, wherein the acrylic base member is formed from a suitable powdered polymeric component and a liquid monomeric component, the liquid component containing a selected fragrancing oil therein.

The fragranced orthodontic appliance of the present invention is prepared by the method comprising the steps of:

admixing an effective amount of fragrancing oil with a liquid monomeric component, wherein the fragrancing oil is chemically stable and non-reactive with the monomeric component;

admixing the resulting fragrance/monomeric liquid with an effective amount of a powdered polymeric component under conditions suitable to initiate further polymerization to form an acrylic base member adapted to conform with an associated palate region of a patient's mouth; and embedding metallic hardware in the acrylic base member such that the embedded hardware extends outward therefrom and contact the patient's teeth when the device is in position in the patient's mouth.

From this process it can be seen that the fragrance permeates the entire appliance. The fragrance is not a coating. The resultant acrylic is homogenous containing the fragrance throughout.

The appliance, when finished, is placed in the mouth in the usual manner. Nothing is required to activate the fragrance. The natural process of saliva flowing across the acrylic portion of the appliance will carry the fragrance to all parts of the mouth and ameliorate the discomfort to the patient due to the pleasant taste and smell.

DESCRIPTION OF THE PREFERRED EMBODIMENT

The present invention is predicated on the discoveries that the use of fragranced acrylic in the production of orthodontic appliances will enhance patient cooperation and that a fragrance imparting material can be successfully integrated homogeneously throughout the acrylic employed in the orthodontic device by admixture with the monomeric component precursor of the acrylic material before it is combined with the associated polymeric component.

The monomeric component and polymeric component suitable for use in the present invention are conventional materials commonly employed in the production of a solid acrylic material with the limitation that the polymeric component employed be a powdered material and the monomer be employed as a liquid.

The monomer used to form an acrylic orthodontic appliance can be fragranced for an individual prosthesis or in larger quantities for resale distribution. The monomer familiar in the art is methylmethacrylate.

The invention pertains to the addition of fragrance oils to methylmethacrylate or other suitable monomer. The fragrance oil employed is a material or materials which have been certified and approved by the United States Food and Drug Administration. Below is a brief list, by way of example only, of suitable fragrance oils which can be used in the present method.

POLYIFF 6071-AR Peppermint
POLYIFF 6072-AR Lemon
POLYIFF 6073-AR Grape
POLYIFF 6074-AR Pineapple
POLYIFF 6075-AR Watermelon These materials are commercially available from International Flavors and Fragrances Corporation.

The fragrance oil should be added to the monomer in a specific ratio. The ratio should not be greater than part fragrance oil to 5 parts monomer or less than 1 part fragrance oil to 10 parts monomer. Compounds should be mixed and stored in a glass container. If too much fragrance oil is used, it will inhibit polymerization. Fragranced monomer can be used immediately or stored for later use.

What is claimed is:

1. An orthodontic appliance for use by a patient comprising:

a hard cold-cured acrylic base member having a suitable fragrancing oil homogeneously dispersed therein, said base member adapted to conform to a preselected palate region located in the patient's mouth; and associated metallic hardware attached to said base member and extending outward therefrom, said hardware being adapted to contact the teeth of the patient located adjacent to said palate region when the appliance is in position in the patient's mouth.

2. The orthodontic appliance of claim 1 wherein said hard cold cured base member is prepared by a method comprising the following steps:

admixing an effective amount of a powdered polymeric precursor to acrylic acid with an effective amount of a liquid monomeric acrylic acid precursor, said monomeric precursor containing a fragrancing oil present in a ration of fragrancing oil to monomer of between 1:5 and 1:10; and allowing said resulting mixture to react and solidify into said base member.

3. The orthodontic appliance of claim 1 wherein the monomeric acrylic acid precursor is methyl methacrylate.

4. A process for making an orthodontic appliance comprising the steps of:

admixing an effective amount of a powdered polymeric precursor of acrylic acid with an effective amount of a liquid monomeric precursor of acrylic acid to form a hard cold curable acrylic material, said liquid monomeric precursor consisting essentially of a monomeric compound reactable with said polymeric compound and a fragrancing oil wherein said fragrancing oil is present in an amount between 1:5 and 1:10, fragrancing oil to monomer respectively;

allowing said admixed material to react to form a solid acrylic material;

conforming said acrylic material to contours of a patient's mouth; and embedding metallic hardware in the acrylic material such that said metallic hardware extends outward therefrom said contacts said patient's teeth when the appliance is placed in position in said patient's mouth.

5. The process of claim 4 wherein the monomeric precursor is methylmethacrylate.

* * * * *